US011375936B2

(12) United States Patent
Chapman et al.

(10) Patent No.: US 11,375,936 B2
(45) Date of Patent: *Jul. 5, 2022

(54) WEARABLE MEDICAL SYSTEM TO MONITOR A PATIENT PARAMETER

(71) Applicant: West Affum Holdings Corp., Grand Cayman (KY)

(72) Inventors: Fred W. Chapman, Renton, WA (US); Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 204 days.

This patent is subject to a terminal disclaimer.

(21) Appl. No.: 16/774,611

(22) Filed: Jan. 28, 2020

(65) Prior Publication Data

US 2020/0155861 A1    May 21, 2020

Related U.S. Application Data

(63) Continuation of application No. 16/011,794, filed on Jun. 19, 2018, now Pat. No. 10,543,375, which is a
(Continued)

(51) Int. Cl.
*A61B 5/25* (2021.01)
*A61N 1/39* (2006.01)
(Continued)

(52) U.S. Cl.
CPC .............. *A61B 5/25* (2021.01); *A61B 5/6831* (2013.01); *A61B 5/6843* (2013.01);
(Continued)

(58) Field of Classification Search
CPC ............................ A61N 1/3918; A61B 5/0408
(Continued)

(56) References Cited

U.S. PATENT DOCUMENTS 3,724,355 A    4/1973    Unger
3,724,455 A    4/1973    Unger
(Continued)

FOREIGN PATENT DOCUMENTS

WO    98/39061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, : loi:10.1093/eurheartj/ehl167, European Society of Cardiology.
(Continued)

*Primary Examiner* — Nadia A Mahmood
(74) *Attorney, Agent, or Firm* — Spectrum IP Law Group LLC

(57) ABSTRACT

A wearable medical system configured to be worn by a person, comprising a support structure configured to be worn by the person, a monitoring device configured to monitor at least one physiological parameter of the person, wherein the at least one physiological parameter includes an electrocardiogram (ECG) reading of the person, an electrode coupled to the support structure, an energy storage device configured to store an electric charge for use in delivering a shock to the person through the electrode, and a biasing mechanism comprising at least one of an inflatable device, a hydraulic device, an electromagnetic device, and/or a screw gun device, the biasing mechanism configured to transition from the unbiased state to the biased state responsive to a value of the at least one physiological parameter reaching a threshold. The electrode is more movable with respect to the person's body in the unbiased state than the biased state.

20 Claims, 8 Drawing Sheets

WEARABLE DEFIBRILLATOR SYSTEM

Related U.S. Application Data continuation of application No. 15/707,896, filed on Sep. 18, 2017, now Pat. No. 10,022,551, which is a continuation of application No. 13/906,327, filed on May 30, 2013, now Pat. No. 9,827,431.

(60) Provisional application No. 61/807,453, filed on Apr. 2, 2013.

(51) Int. Cl.
*A61B 5/00* (2006.01)
*A61B 7/00* (2006.01)
*A61B 5/0205* (2006.01)

(52) U.S. Cl.
CPC ......... *A61N 1/3904* (2017.08); *A61N 1/3918* (2013.01); *A61N 1/3993* (2013.01); *A61B 5/0205* (2013.01); *A61B 7/00* (2013.01)

(58) Field of Classification Search
USPC .......................................................... 607/4, 7
See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,425,749 A | 6/1995 | Adams |
| 5,474,574 A | 12/1995 | Payne et al. |
| 5,528,449 A | 6/1996 | Koch |
| 5,630,834 A | 5/1997 | Bardy |
| 5,662,690 A | 9/1997 | Cole et al. |
| 5,782,878 A | 7/1998 | Morgan et al. |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,141,588 A | 10/2000 | Cox et al. |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motli et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,473,638 B2 | 10/2002 | Ferek-Petric |
| 6,529,875 B1 | 3/2003 | Nkajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 6,941,168 B2 | 9/2005 | Girouard |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valemtine |
| 7,974,689 B2 | 7/2011 | Volpe et al. |
| 8,086,320 B2 | 12/2011 | Benjamin |
| 8,135,462 B2 | 3/2012 | Owen et al. |
| 8,140,154 B2 | 3/2012 | Donnelly et al. |
| 8,271,082 B2 | 9/2012 | Donnelly et al. |
| 8,323,189 B2 | 12/2012 | Tran et al. |
| 8,369,944 B2 | 2/2013 | Macho et al. |
| 8,437,824 B2 | 5/2013 | Moon et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,757,579 B2 | 9/2017 | Foshee et al. |
| 9,827,431 B2 | 11/2017 | Chapman et al. |
| 10,022,551 B1 | 7/2018 | Chapman et al. |
| 10,426,966 B2 | 10/2019 | Foshee et al. |
| 10,543,375 B2 | 1/2020 | Chapman et al. |
| 2003/0158593 A1 | 8/2003 | Heilman et al. |
| 2004/0220623 A1 | 11/2004 | Hess |
| 2005/0107833 A1 | 5/2005 | Freeman et al. |
| 2005/0107834 A1 | 5/2005 | Freeman et al. |
| 2006/0017575 A1 | 1/2006 | McAdams |
| 2007/0179539 A1 | 8/2007 | Degroot et al. |
| 2008/0312708 A1 | 12/2008 | Volpe et al. |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2009/0076559 A1 | 3/2009 | Libbus et al. |
| 2009/0326339 A1 | 12/2009 | Horvitz |
| 2010/0007413 A1 | 1/2010 | Herleikson |
| 2010/0298899 A1 | 11/2010 | Donnelly et al. |
| 2010/0331904 A1 | 12/2010 | Warren et al. |
| 2011/0022105 A9 | 1/2011 | Owen et al. |
| 2011/0288604 A1 | 11/2011 | Kaib et al. |
| 2011/0288605 A1 | 11/2011 | Kalib et al. |
| 2012/0109687 A1 | 5/2012 | Tubb |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158074 A1 | 6/2012 | Hall |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0012151 A1 | 1/2013 | Hankins |
| 2013/0218252 A1 | 8/2013 | Kaib et al. |
| 2013/0085538 A1 | 9/2013 | Volpe et al. |
| 2013/0231711 A1 | 9/2013 | Kaib et al. |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinolli-Buitoni et al. |
| 2014/0073979 A1 | 3/2014 | Inciardi et al. |
| 2014/0088739 A1 | 3/2014 | Ellis et al. |
| 2014/0091937 A1 | 4/2014 | Pratt |
| 2014/0150781 A1 | 6/2014 | DiCapura et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee et al. |

OTHER PUBLICATIONS

Lifecor LifeVest System Model WCD 3100 Operator's Manual, 2006, PN 20B0040 Rev Fl, Zoll Lifecor Corporation, Pittsburgh, PA.

(56) References Cited

OTHER PUBLICATIONS

LifeVest Model 4000 Patient Manual, Zoll, 2009, PN 20B0047 Rev B.
Heartstart MRx and XL AED Algorithm—Application Nole, Jul. 2001, Edition 2 Philips Healthcare, USA.
The LifeVest Network/Patient Data Management System, Zoll, 2015, 20C0503 Rev A.
Pagan-Carlo, et al., "Encircling Overlapping Multipulse Shock Waveforms for Transthoracic Defibrillation," JACC Journals, Dec. 1998, vol. 32 Issue 7, p. 2065-2071.

FIG. 1   *WEARABLE DEFIBRILLATOR SYSTEM*

*SAMPLE THRESHOLDS FOR MAKING DECISIONS*

COMPONENTS OF EXTERNAL DEFIBRILLATOR

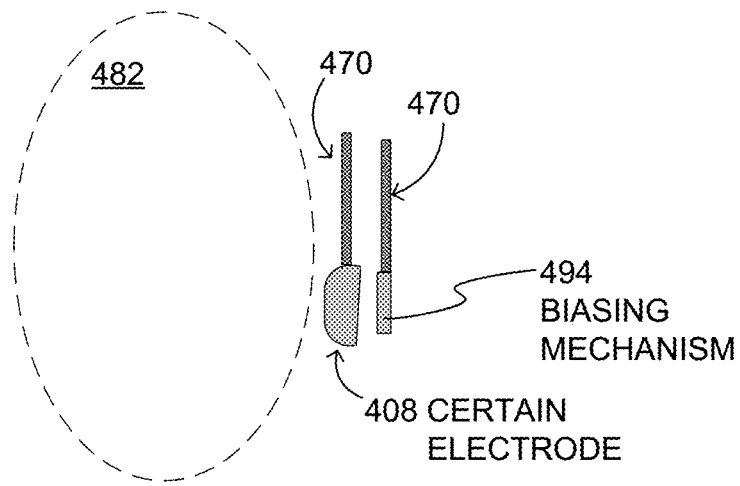
FIG. 4A  *ELECTRODE UNBIASED TOWARDS BODY*
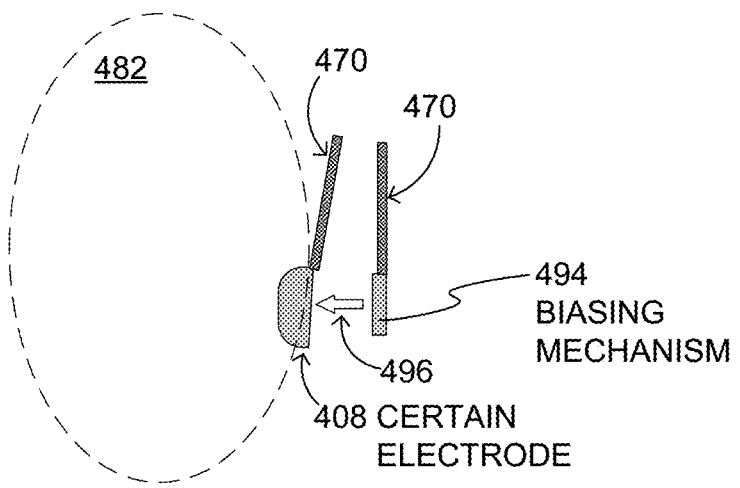
FIG. 4B  *ELECTRODE BIASED TOWARDS BODY*

*METHODS*

*METHOD OPERATIONS*

700
| 747 RECORD INDICATION OF ELECTRODE BECOMING BIASED |
FIG. 7   *METHOD OPERATIONS*
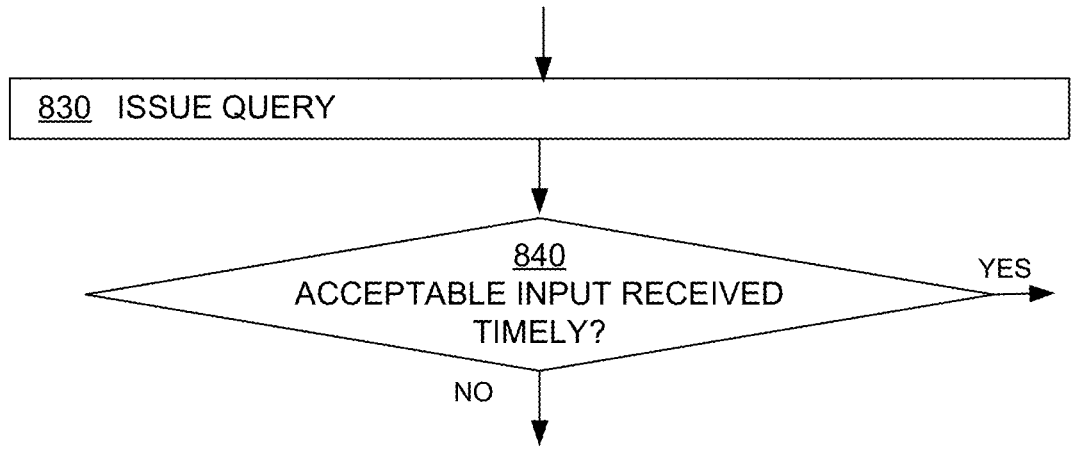
FIG. 8   *METHOD OPERATIONS*

*METHODS*

METHODS

WEARABLE MEDICAL SYSTEM TO MONITOR A PATIENT PARAMETER

CROSS REFERENCE TO RELATED PATENT APPLICATIONS

The present application is a continuation of U.S. application Ser. No. 16/011,794 filed Jun. 19, 2018 (pending), which in turn is a continuation of U.S. application Ser. No. 15/707,896 filed Sep. 18, 2017, now U.S. Pat. No. 10,022,551, which in turn is a continuation of U.S. application Ser. No. 13/906,327 filed on May 30, 2013, now U.S. Pat. No. 9,827,431. Said application Ser. No. 13/906,327 claims the benefit of U.S. Provisional Patent Application Ser. No. 61/807,453 filed on Apr. 2, 2013. Said application Ser. No. 16/011,794, said application Ser. No. 15/707,896, said application Ser. No. 13/906,327, and said Application No. 61/807,452 are hereby incorporated by reference in their entireties.

BACKGROUND

Some types of heart arrhythmia may result in lessening blood flow, thus reducing the amount of blood pumped to the various parts of the body. Some arrhythmias may even result in a Sudden Cardiac Arrest (SCA). SCA leads to death very quickly, unless treated in the interim.

People who have had a heart attack have an increased risk of SCA, and therefore it is recommended that they receive an Implantable Cardioverter Defibrillator ("ICD"). An ICD has electrodes that continuously monitor the person's electrocardiogram ("ECG"). If certain types of heart tachyarrhythmia are detected, then the ICD delivers electrical therapy through the heart.

People with increased risk of an SCA are sometimes given a wearable external defibrillator system. The recipients typically include those who have had a heart attack but have not yet had an ICD implanted. A wearable defibrillator system typically includes a vest or harness that is worn by the person. The system includes a defibrillator and electrodes that are attached to the vest or harness. Typically the system monitor the person's ECG via the electrodes continuously. If a heart tachyarrhythmia is detected, then the defibrillator delivers the appropriate electrical discharge through the heart.

A problem is that compliance by the person is often not full. While the person has the system, they often do not wear it because they find it cumbersome and uncomfortable. The issue of improving compliance has been addressed, for example in US Patent Application No. 2012/0283794.

A root of the discomfort is from the fact that the electrodes of the wearable system have to be making good electrical contact continuously with the person's skin, so that the person's ECG can be monitored continuously. The problem has been addressed, for example in U.S. Pat. No. 6,546,285, titled LONG TERM WEAR ELECTRODE FOR DEFIBRILLATION SYSTEM. The latter patent teaches, among other things, to move the electrodes to different places on the person's skin at different times, and/or to use a hydrogel for the electrodes that includes a therapeutic agent which promotes skin health.

BRIEF SUMMARY

The present description gives instances of wearable defibrillator systems and methods, the use of which may help overcome problems and limitations of the prior art.

In one embodiment, a wearable defibrillator system includes a support structure with one or more electrodes in an unbiased state. A monitoring device monitors, for the long term, a parameter of the person that is not the person's ECG; rather, the monitored parameter can be the person's motion, or a physiological parameter. When a value of the monitored parameter reaches a threshold, such as when the person is having an actionable episode, the electrode becomes mechanically biased against the person's body, for making good electrical contact. Then, if necessary, the person can be given electrical therapy, such as defibrillation.

An advantage over the prior art is that, while the wearable defibrillator system does require long-term wearing to protect the person, wearing itself does not require that one or more of its electrodes be making good electrical contact with the person's skin for the long term. The contact is made by the biasing, when the system otherwise detects that the person is having an actionable episode. Until then, however, the electrodes can be worn more loosely, sometimes similarly with how loose the other garments feel to the wearer. This can reduce the person's aversion to wearing the defibrillation system, who might in turn comply more with the instruction to wear it.

These and other features and advantages of this description will become more readily apparent from the following Detailed Description, which proceeds with reference to the drawings, in which:

BRIEF DESCRIPTION OF THE DRAWINGS

FIG. 4A is a diagram showing an electrode, such as a possible embodiment of an electrode of FIG. 1, which is not being biased towards the body of the wearer according to embodiments.

FIG. 4B is a diagram showing the electrode of FIG. 4A, but in which the electrode is instead being biased towards the body of the wearer according to embodiments.

FIG. 7 is a flowchart segment for describing an additional optional operation according to embodiments.

FIG. 8 is a flowchart segment for describing additional optional operations according to embodiments.

DETAILED DESCRIPTION

As has been mentioned, the present description is about wearable defibrillator systems and methods. Embodiments are now described in more detail.

Embodiments include wearable defibrillator systems, which are configured to be worn by a person. The person is sometimes called also a patient and/or a wearer. The person wearing the system may be moving, for example during their daily activities. As they move, any garments they wear may shift with respect to their body. The wearable defibrillator systems of the embodiments are configured to defibrillate the person by delivering electrical charge to the person's body.

Systems according to embodiments may include a support structure, which is configured to be worn by the person. The support structure can be any structure suitable for wearing, such as a harness, a vest, a garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the weight of the defibrillator.

Figure 1:
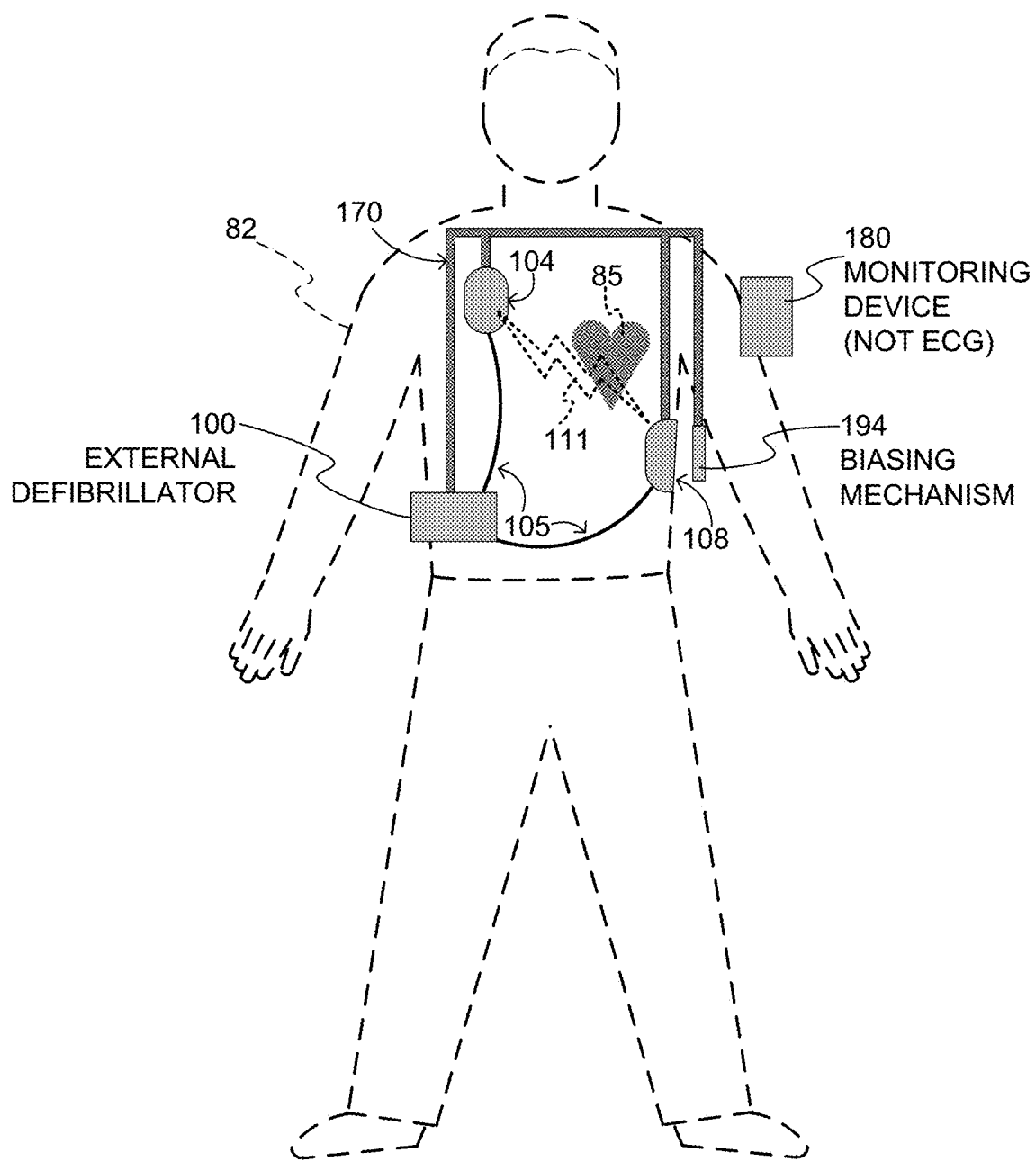
FIG. 1 is a diagram of components of a wearable defibrillator system, according to embodiments.

FIG. 1 is presented as an example of only some embodiments. FIG. 1 is a diagram of components of a wearable defibrillator system. A generic support structure 170 is shown relative to the body of a person 82. Structure 170 could be a harness, vest, garment, and so on. It could be implemented in a single component, or multiple components, as per the above. Structure 170 is wearable by person 82, but the manner of wearing it is not depicted, as structure 170 is depicted only generically in FIG. 1.

Systems according to embodiments may also include a monitoring device, which can be used for determining whether intervention by the system will be necessary. By way of an example, a monitoring device 180 is also shown in FIG. 1. Optionally, the monitoring device is coupled to the support structure, physically and/or in terms of electrical communication with other elements coupled to the support structure, as will be deemed necessary by a person skilled in the art in view of this disclosure.

The monitoring device is configured to monitor at least one parameter of the person, which is not an electrocardiogram ("ECG") of the person. The monitoring device generates a signal that encodes a value of the monitored parameter. The value of the parameter can be used by the system as will be deemed necessary by a person skilled in the art in view of this disclosure.

The value of the parameter, in turn, can be used to make a decision. The decision can be made when a threshold is reached or exceeded. The determination of whether the threshold is reached or exceeded can be made as is known in the art. For example, in embodiments where a value is encoded in a voltage level, the determination can be made by a comparator that is tripped when the voltage level exceeds the applicable threshold voltage level. In other embodiments, the system can optionally include a logic device, such as a processor, and the value is encoded in as a number. The logic device can be is configured to determine when the parameter has reached or exceeded the appropriate threshold. Different thresholds according to embodiments are now described, both for the parameter of the monitoring device, and other parameters.

Figure 2:
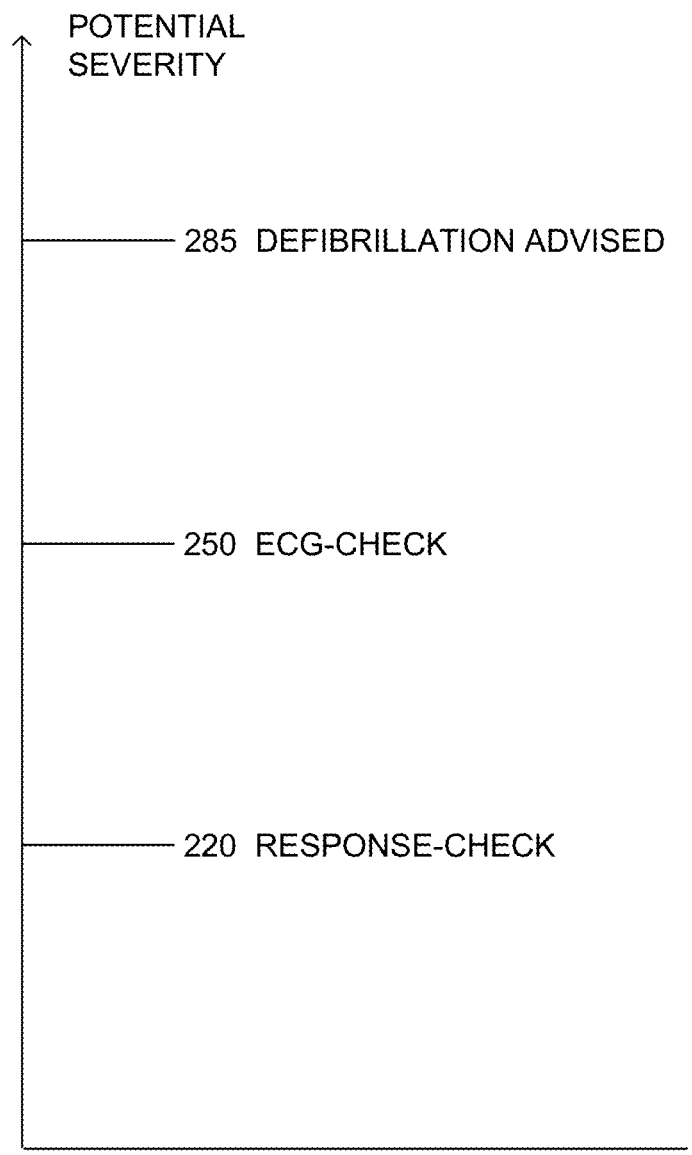
FIG. 2 is a diagram showing sample thresholds for making decisions according to embodiments.

FIG. 2 is a diagram showing possible thresholds 220, 250, 285 for making decisions according to embodiments. Examples of use of these thresholds are described later in this document, also in terms of flowcharts. It will be appreciated that not all of these thresholds are used in every embodiment.

Thresholds 220, 250, 285 are shown on a single scale, according to relative potential severity of the patient's condition. Even though shown in a single scale, it should be remembered that these thresholds may be established for the same or different patient parameters, for use by the same or different elements of embodiments. For example, the thresholds can be either for the parameter monitored by the monitoring device, or by another monitoring device, or for an ECG reading of the person obtained by electrodes, and so on. Moreover, there can be same or different results if the thresholds are reached or exceeded.

The thresholds of FIG. 2 are shown in a scale. Embodiments escalate the checking and operations, such as along this scale, as they detect the patient's condition to be more severe, in ways that the system could address by administering electrical therapy.

These thresholds are now described in more detail. Threshold 220 is a response-check threshold, above which the decision can be that the person be asked to respond, in some manner, as to whether they are fine. A person who responds they are fine will likely not need electrical therapy at this time. Threshold 250 is an ECG-check threshold, above which the decision can be that an ECG reading of the person needs to be taken for certainty. If the person's ECG turns out to be a non-shockable rhythm, such as a normal sinus rhythm, then the system need not administer electrical therapy. Threshold 285 is a defibrillation advised threshold, above which a defibrillate decision is made, and the person is defibrillated. Below the lowest of thresholds, which in FIG. 2 is threshold 220, the patient can be presumed to be not in danger, and the decision can be that no action is taken, and there is no escalation.

Returning now to the monitoring device, its monitored parameters can be a motion of the person's body, in some embodiments. In these embodiments, the monitoring device may include a motion detector, which can be made in many ways as is known in the art. Or, the monitoring device could include a GPS, which informs of the location, and the rate of change of location over time. Many motion detectors output a motion signal that is indicative of the motion of the detector, and thus of the person's body.

It is known how to infer the activities and likely severity of the patient condition by interpreting the motion signals. For example, if the person stops moving at a time when they are expected to be moving or continue moving or exhibits other behavior that indicates that SCA may be taking place, that can be cause for escalation, as per the above. As such, the threshold can sometimes be adjusted according to an output of the motion detector itself.

The thresholds can be adjusted also with regard to additional parameters that can be monitored. One such additional parameter can be the time of day, which can be monitored by a clock in a processor of the system. For example, the person is expected to be sleeping during more of the night hours.

In other embodiments, the monitored parameter is a physiological parameter of the person. The physiological parameter can be anyone that would help detect whether the person is in need of electrotherapy by the wearable defibrillation system. Example such parameters include the person's blood oxygen level, blood flow, blood pressure, blood perfusion, pulsatile change in light transmission or reflection properties of perfused tissue, heart sounds, breathing sounds and pulse. Accordingly, the monitoring device could be a pulse oximeter, a Doppler device for detecting blood flow, a cuff for detecting blood pressure, illumination detectors and maybe sources for detecting color change in tissue, a device that can detect artery wall movement, a device with a microphone, and so on. Pulse detection is taught at least in Physio-Control's U.S. Pat. No. 8,135,462, which is hereby incorporated by reference in its entirety. In addition, a person skilled in the art may implement other ways of performing pulse detection. Similarly with motion, if the monitored physiological parameter indicates that SCA could be taking place, that can be cause for a decision to check further or defibrillate, and so on.

In yet other embodiments, both the person's physiological parameter and motion can be monitored in combination. The value of the physiological parameter becomes better informed from the motion profile, as is the appropriate threshold for determining whether an actionable episode is taking place so as to escalate. The threshold can be adjusted accordingly. For example, if the person is running then a somewhat higher pulse rate may be tolerated until a time after they stop, without needing to escalate, and so on.

Systems according to embodiments may also include a capacitor, which can be configured to store an electrical charge. Under certain circumstances, the charge is configured to be delivered to the person's body according to embodiments. Preferably the capacitor is coupled to the support structure, and the charge is delivered while the person is wearing the support structure.

In certain embodiments, the capacitor is implemented as part of a defibrillator, such as sample external defibrillator 100 in FIG. 1. In those cases, the defibrillator can be coupled to the support structure, such as defibrillator 100 is coupled to structure 170 in FIG. 1. In other embodiments, a full defibrillator may not be implemented, such as in instances where the capacitor charge is controlled to be delivered to the person remotely, and so on.

Figure 3:
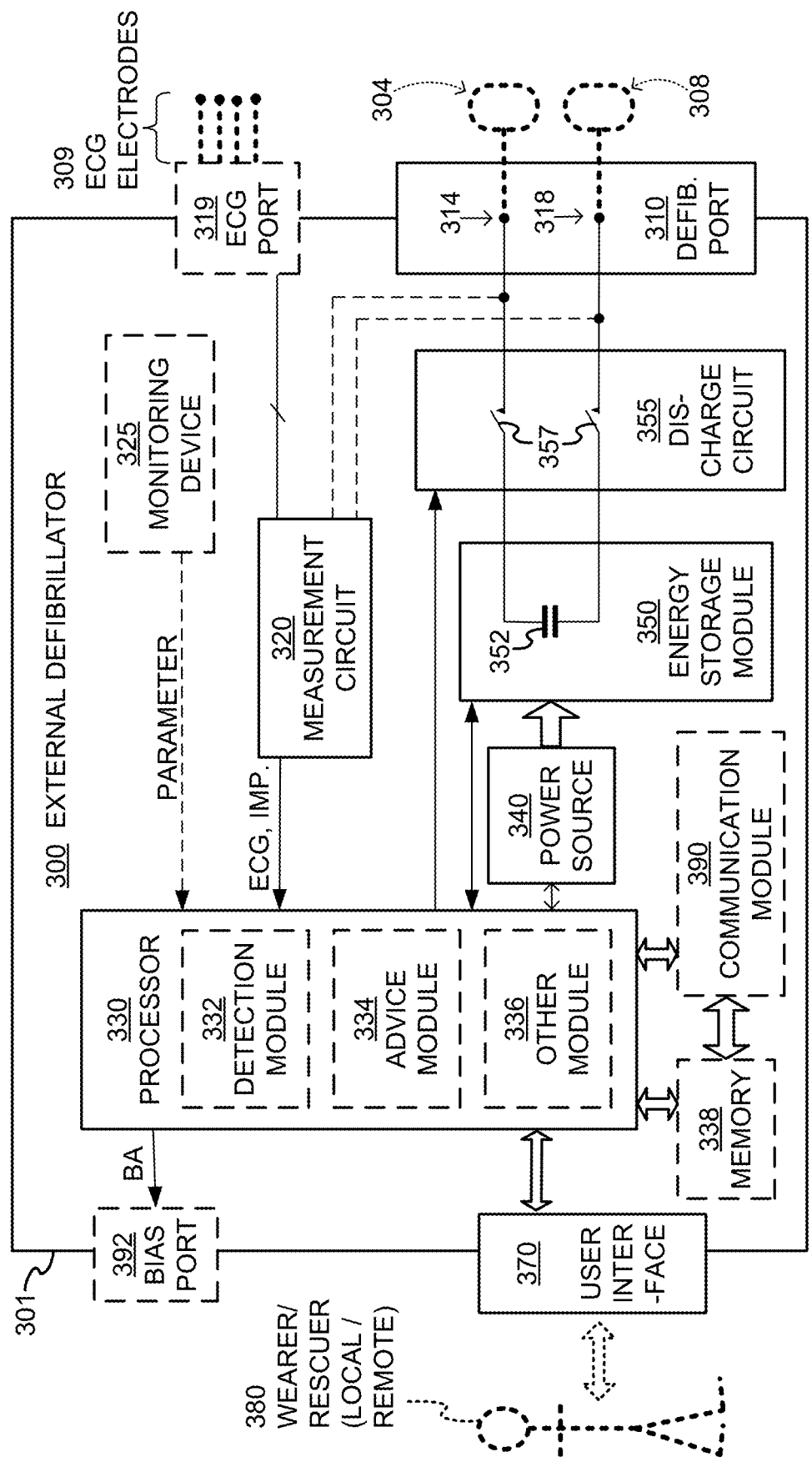
FIG. 3 is a diagram showing components of an external defibrillator, such as the one shown in FIG. 1, which is made according to embodiments.

FIG. 3 is a diagram showing components of an external defibrillator 300 made according to embodiments. These components can be, for example, in external defibrillator 100 of FIG. 1, in the event that defibrillator components beyond the capacitor are provided. These components of FIG. 3 can be provided in a housing 301, which is also known as casing 301.

External defibrillator 300 is intended for person 380 who would be the wearer, such as person 82 of FIG. 1. In some embodiments, defibrillator 300 includes the above described monitoring device 325, which can include any one of a motion sensor, a physiological parameter motion, etc., as per the above. In other embodiments, the monitoring device is provided outside housing 301, such as monitoring device 180 is shown in the example of FIG. 1.

Defibrillator 300 typically includes a defibrillation port 310, such as a socket in housing 301. Defibrillation port 310 includes nodes 314, 318. Defibrillation electrodes 304, 308, which will be described later in more detail, can be plugged in defibrillation port 310, so as to make electrical contact with nodes 314, 318, respectively. It is also possible that defibrillation electrodes can be connected continuously to defibrillation port 310, instead. Either way, defibrillation port 310 can be used for guiding via electrodes to the wearer the electrical charge that has been stored in energy storage module 350.

Defibrillator 300 may optionally also have an ECG port 319 in housing 301, for plugging in ECG electrodes 309, which are also known as ECG leads. It is also possible that ECG electrodes can be connected continuously to ECG port 319, instead. ECG electrodes 309 can help sense an ECG signal, e.g. a 12-lead signal, or a signal from a different number of leads, as long as they make good electrical contact with the body of the patient.

Defibrillator 300 also includes a measurement circuit 320. Measurement circuit 320 receives physiological signals from ECG port 319, if provided. Even if defibrillator 300 lacks ECG port 319, measurement circuit 320 can obtain physiological signals through nodes 314, 318 instead, when defibrillation electrodes 304, 308 are attached to the patient.

In these cases, a person's ECG signal can be sensed as a voltage difference between electrodes 304, 308. Plus, impedance between electrodes 304, 308 can be sensed for detecting, among other things, whether these electrodes 304, 308 are not making good electrical contact with the person's body. These physiological signals are sensed, and information about them is rendered by circuit 320 as data, or other signals, etc.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332. Processor 330, running detection module 332, is a sample embodiment of a logic device configured to determine whether the above-described monitored parameter has reached a specific threshold. For example, the monitoring parameter can be input from monitoring device 325, if provided. For another example, detection module 332 can include a ventricular fibrillation ("VF") detector and the person's sensed ECG from measurement circuit 320 can be used to determine whether the person is experiencing VF. Detecting VF is useful, because VF is a precursor to SCA.

Another such module in processor 330 can be an advice module 334, which arrives at advice, for example based on outputs of detection module 332, and/or implements decisions. There can be many types of advice according to embodiments. As one example, a Shock Advisory Algorithm can render the advice to shock, as opposed to not shock the person. Such can be, for example, when the person's condition has reached or exceeded defibrillation advised threshold 285 of FIG. 2. Shocking can be for defibrillation, pacing, and so on. If the advice is to shock, some external defibrillator embodiments proceed with shocking, or may advise a remote attendant to do it, and so on. As another example, the advice can be to administer CPR, and defibrillator 300 may further issue prompts for it, and so on.

One more example of a decision that can be made is to bias one or more electrodes towards the person's body, as will be described later in this document. The decision can be communicated in some of these embodiments by generating a biasing signal BA. Defibrillator 300 optionally includes also a bias port 392 for exporting biasing signal BA from bias port 392 to a biasing mechanism of the system, which will also be described later.

Processor 330 can include additional modules, such as module 336, for other functions. In addition, if monitoring device 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330 and can also include protocols and ways that decisions can be made by advice module 334. In addition, memory 338 can store prompts for person 380, if they are a local rescuer. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes a capacitor 352, which can be a single capacitor or a system of capacitors, and so on. As described above, capacitor 352 can store the charge for delivering to the patient.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for a user 380. User 380 can be the wearer, if conscious, or a rescuer. The rescuer can be local, such as a bystander who might offer assistance, or a trained person who might arrive after the fact. Alternately the rescuer could be remote, such as a trained person in remote communication with a system according to embodiments, and/or with the wearer.

User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, touchscreens, a microphone, and so on. In addition, discharge circuit 355 can be controlled by processor 330, or directly by user 380 via user interface 370, and so on.

Defibrillator 300 can optionally include other components. For example, a communication module 390 may be provided for communicating with other machines or a remote rescuer 380. Such communication can be performed wirelessly, or via wire, or by infrared communication, and so on. This way, data can be communicated, such as patient data, episode information, therapy attempted, CPR performance, and so on.

Embodiments of the system of the invention may additionally include defibrillation electrodes. It will be appreciated that the defibrillation electrodes of embodiments could both deliver a charge, and also serve for sensing the person's ECG. The defibrillation electrodes can deliver to the person electrical charge stored in the capacitor, for restoring their heart rhythm, when the defibrillation electrodes make good electrical contact with the body of the wearer.

FIG. 1 shows an example of defibrillation electrodes 104, 108, which are coupled to external defibrillator 100 via electrode leads 105. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock, goes also through heart 85, in an attempt to restart it, for saving the life of person 82.

In the example of FIG. 3, defibrillation electrodes 304, 308 would plug into defibrillation port 310, so as to make electrical contact with nodes 314, 318, respectively. Defibrillation electrodes 304, 308 could be similar to defibrillation electrodes 104, 108 of FIG. 1.

Embodiments of the system of the invention may additionally include ECG electrodes. If provided, ECG electrodes could be electrically connected for example as seen in FIG. 3 for ECG electrodes 309.

As such, in many embodiments, either defibrillation electrodes are provided by themselves, or ECG electrodes are provided in addition to defibrillation electrodes. An ECG reading can be provided by either type of electrodes, preferably while they are making good electrical contact with the body of the person, and more particularly the skin.

In a number of embodiments, all the above mentioned electrodes are not always making good electrical contact with the person's skin. In fact, at least one of the above-mentioned electrodes, also known as a certain electrode, can be coupled to the support structure such that, while the support structure is worn by the person, the certain electrode is at a so-called unbiased state. When in the unbiased state, the certain electrode is moveable with respect to the person's body, for example as a result of the person's moving around. For example, the certain electrode could contact the person's skin as a regular garment does, for example as does a shirt that is not tightened around the person's body. As such the certain electrode could shift around the person's skin, and occasionally lose contact with it. In those occasional moments, the electrical impedance between the certain electrode and the patient's skin would become infinite.

As will be seen below, the certain electrode can be either one of the defibrillation electrodes, or one of the ECG electrodes, if provided. Of course, what is written about the certain electrode could also apply for a companion electrode that performs a similar function.

It is that lack of the certain electrode's making consistently good electrical contact with the skin that makes the support structure more comfortable to wear than the prior art for the long term. Of course, the certain electrode not necessarily making consistently good electrical contact for the long term is not desirable, but that will be addressed by the biasing mechanism that is now described.

Embodiments of the system of the invention may additionally include a first biasing mechanism. The first biasing mechanism can be configured to cause the certain electrode to transition from the above described unbiased state to a so-called biased state. When in the biased state, the certain electrode is biased towards the person's body against the support structure. The biasing, then, is by a force that causes the certain electrode to be less moveable with respect to the person's body than when in the unbiased state. As such, when in the biased state, the certain electrode makes better and/or more reliable electrical contact with the person's skin than in the unbiased state. The better electrical contact can be used for more reliable defibrillation and or receiving ECG signals, as the case may be for the certain electrode.

In preferred embodiments, the first biasing mechanism can cause the certain electrode to transition from the unbiased state to the biased state, responsive to a value of the monitored parameter reaching a threshold. As such, the first biasing mechanism can be configured to receive a biasing signal that signifies that the determination has been made that the value of the monitored parameter has reached the applicable threshold, and there will be escalation. For example, when a logic device has been provided to make that determination, the first biasing mechanism can be configured to receive the biasing signal from that logic device. An example was described above for biasing signal BA from the device of FIG. 3.

The transitioning from the biased state to the unbiased state is also called biasing and deployment of the certain electrode. Deployment is for the certain electrode, and possibly also other electrodes of the system. It will be appreciated that deployment in this sense might not necessarily change much the position of the certain electrode with respect to the patient's body, but it will change the force with which it is pushed or biased towards the body.

The first biasing mechanism can be made in any way so as to cause pressure to be applied to the certain electrode against the support structure, and therefore bias the certain electrode towards the person's body. Various embodiments of the first biasing mechanism include a spring that is released, causing the support structure to be tightened around the body, causing a balloon to be inflated, adding pressure to a hydraulic system, applying force such as with an electromagnet, and turning a screw gun arrangement so that turning result in a translation motion. The sample embodiment of FIG. 1 shows also a biasing mechanism 194.

A sample deployment is now described. FIG. 4A is a diagram according to an embodiment. A patient 482 is wearing a support structure 470, of which two portions are shown. Support structure 470 is made according to embodiments and, as with FIG. 1, it is shown only generically. A certain electrode 408 could be either a defibrillation electrode or an ECG electrode and is coupled to support structure 470 in an unbiased state. In the instant of FIG. 4A, certain electrode 408 does not even contact the skin of patient 482. A biasing mechanism 494 is also coupled to support structure 470.

FIG. 4B is a diagram showing the same elements as FIG. 4A, except that biasing mechanism 494 exerts a biasing force 496 due to which certain electrode 408 is biased towards patient 482 against support structure 470. In the instant of FIG. 4B, certain electrode 408 contacts the skin of patient 482. Certain electrode 408 is less easily movable in FIG. 4B than in FIG. 4A.

In a number of embodiments, the first biasing mechanism is preferably made so that it is further reversible, either by the wearer, or by a bystander, or by a remotely monitoring medical professional. Reversing would be upon verifying that there is no actionable episode to be addressed by the system, moves downwards in the scale of FIG. 2, and is the opposite of escalation. Reversing could be automatically enabled by further functionality. Or, reversing could be implemented by permitting the mechanically reverse motion of what deployed the certain electrode and any other electrodes. Care should be taken that reversing is not suggested prematurely, or by a person who does not understand the function of the system, such as a well-meaning by uninformed bystander.

It will be appreciated that, when the certain electrode is in the biased state, it can be counted on to make better electrical contact with the body. Accordingly, any ECG inputs received by the certain electrode preferably are trusted more when the certain electrode is in the biased state than in the unbiased state. Regardless, in a preferred embodiment, an additional, serendipitous check on the patient can be an ECG reading that is received incidentally while the certain electrode is in the unbiased state and whose content causes alarm. Such an ECG reading can be used in a number of ways, for tentative escalation. One example is for the biasing mechanism to cause the certain defibrillation electrode to transition to the biased state from the unbiased state responsive to an ECG reading of the person that is received incidentally while the certain electrode is in the unbiased state.

In most embodiments, the certain electrode makes good electrical contact while biased, i.e. while the biasing mechanism exerts a biasing force. In some embodiments, however, the certain electrode includes adhesive material. The adhesive material can be always there or be deployed right before the biasing. As the biasing mechanism causes the certain electrode to transition from the unbiased state to the biased state by exerting the biasing force, it in turn causes the certain electrode to adhere to the person due to the adhesive material. The electrode can remain adhered even if the biasing mechanism discontinues exerting the biasing force.

Embodiments of the system of the invention may additionally include a memory. The memory can be configured to record various aspects, such as values of the parameter being monitored, an event of a threshold having been reached by the monitored parameter, an event of the certain electrode transitioning to the biased state form the unbiased state, and so on. In embodiments where the defibrillator of FIG. 3 is used, the memory can be memory 338.

Embodiments of the system of the invention may further include a user interface. The user interface can include output devices, such as a speaker, a display, a vibration mechanism etc., plus input devices such as a microphone, buttons, keys, and other implements that a user can activate or deactivate. The user interface can be configured to issue a query to the person, to verify that they are conscious, and therefore confirm there is no cause for alarm from a detected value of the monitored parameter. Such can be, for example, when the person's condition has reached or exceeded response-check threshold 220 of FIG. 2. In those instances, embodiments permit the wearer to enter an input in response to the query within a certain time, before the certain electrode transitions from the unbiased state to the biased state. An example is a "live man switch", which the wearer can push, to indicate they are fine. In such embodiments, the certain electrode can be configured to transition to the biased state only if a preset acceptable input has not been received in response to the query within a preset time after the query has been issued. In embodiments where the defibrillator of FIG. 3 is used, the user interface can be user interface 370.

If the option of querying the user is indeed provided, it can be further coupled with the advent of a serendipitous receipt of an ECG reading whose content causes alarm while the certain electrode is in the unbiased state. In such embodiments, the user query can be triggered as above.

As mentioned above, in some embodiments, the certain electrode is a defibrillation electrode. In these embodiments, the electrical charge stored in the capacitor of the system is configured to be delivered through the person's body via the certain electrode, and also via another defibrillation electrode. In the particular example of FIG. 1, defibrillation electrode 108 is the certain electrode, and defibrillation electrode 104 is the other defibrillation electrode, while no separate ECG electrodes are provided. Certain electrode 108 can become deployed, as can electrode 104 by a suitable biasing mechanism.

Moreover, in other embodiments, the certain electrode can be an ECG electrode. In these embodiments, one or more ECG electrodes are thus provided above and beyond defibrillation electrodes. The one or more ECG electrodes can become deployed, as per the above.

When ECG electrodes are also provided, there are a number of options about the defibrillation electrodes. One option is for the defibrillation electrodes to be always attached to the patient by how they are coupled to the support structure. This is not very advantageous, however, as the intent is to liberate the person from contact with electrodes for the long-term wear, so as to make compliance more palatable.

Another option is to have the defibrillation electrodes also be deployable. More particularly, the defibrillation electrodes can be coupled to the support structure. The coupling can be such that, while the support structure is worn by the person, at least a particular one of the defibrillation electrodes is either at an unbiased state or a biased state. Similarly, with the above, when the particular defibrillation electrode is in the unbiased state, it is moveable with respect to the person's body responsive to the person's moving. Moreover, when the particular defibrillation electrode is in the biased state, the particular defibrillation electrode is biased towards the person's body against the support structure so as to be less moveable with respect to the person's body than when in the unbiased state.

When the defibrillation electrodes are also deployable, an ECG reading can advantageously be received also from the particular electrode that is deployed. Moreover, it is preferred to configure the electrical charge to be delivered through the person's body when the particular defibrillation electrode is in the biased state, when defibrillation advised threshold 285 is exceeded. In fact, it is even more preferred to configure the electrical charge to be delivered through the person's body only when the particular defibrillation electrode is in the biased state, to avoid wasting energy, or misdirecting the electrical charge.

When the defibrillation electrodes are also deployable, there are a number of embodiments. An embodiment is for at least one of the ECG electrodes to be attached to at least one of the defibrillation electrodes. As such, deploying the certain ECG electrode by the first biasing mechanism also deploys the defibrillation electrode. Attachment can be implemented in any number of ways. For example, the ECG electrode can be formed integrally with one of the defibrillation electrodes. In a preferred embodiment, the ECG electrode can be formed as a segmented electrode with a defibrillation electrode. In this option, the certain electrode can also be considered to be the defibrillation electrode, which has the further feature of one or more ECG electrodes attached to it.

Another embodiment is for at least one of the defibrillation electrodes to be truly distinct from the ECG electrodes. This option has the advantage that certain types of false alarm will result in deploying only the ECG electrodes upon partial escalation, but not the usually larger defibrillation electrodes. This option also has the disadvantage that two deployments may be needed, which requires more biasing structures in the system.

In such embodiments, a second biasing mechanism can be provided for the system, which is distinct from the first biasing mechanism. The second biasing mechanism can be configured to cause the particular defibrillation electrode to transition from its unbiased state to its biased state.

Methods are now described, by using flowcharts. These methods may also be practiced with additional operations, and by embodiments described above. These methods are for a defibrillator system that is wearable by a person who may be moving, and which includes a support structure and electrodes coupled to the support structure. The electrodes are coupled such that, while the support structure is worn by the person, at least a certain one of the electrodes is moveable with respect to the person's body responsive to the person's moving. The certain electrode can be a defibrillation electrode, an ECG electrode, or a combination of the two. Moreover, these flowcharts may find more detailed explanations in what is written above.

Figure 5:
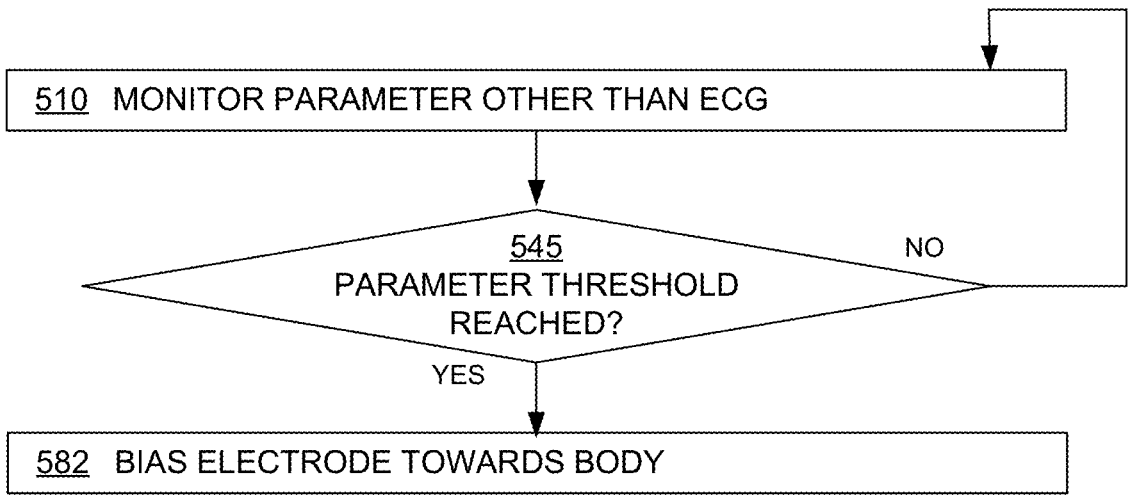
FIG. 5 is a flowchart for illustrating methods according to embodiments.

FIG. 5 shows a flowchart 500 for describing methods according to embodiments. According to an operation 510, at least one parameter of the person is monitored, while the person is wearing the support structure. The parameter is not an electrocardiogram ("ECG") of the person. In some embodiments, the parameter is a motion of the person's body. In other embodiments, the parameter is a physiological parameter, which could be one of the person's blood perfusion, blood flow, blood pressure, blood oxygen level, pulsatile change in light transmission/reflection properties of perfused tissue, heart sounds and breathing sounds.

According to a next operation 545, it is determined whether a threshold has been reached for the monitored parameter. If not, execution returns to operation 510.

If yes, then according to a next operation 582, the certain electrode becomes biased towards the person's body against the support structure. Accordingly, the certain electrode becomes less moveable with respect to the person's body than previously. Biasing can be by exerting force, with implements such as described above.

Figure 6:
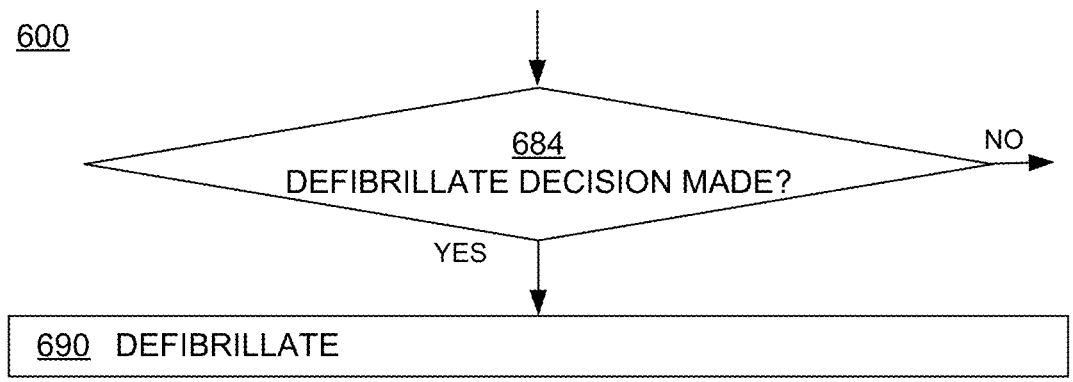
FIG. 6 is a flowchart segment for describing additional optional operations according to embodiments.

FIG. 6 shows a flowchart segment 600 for describing additional optional operations according to embodiments. The additional optional operations of flowchart segment 600 can be added to other flowcharts in this description.

According to an optional operation 684, it is inquired whether a defibrillate decision has been made. If not, execution can return to a previous operation. If yes, then according to a next operation 690, the person is defibrillated.

FIG. 7 shows a flowchart segment 700 for describing additional optional operations according to embodiments. The additional optional operations of flowchart segment 700 can be added to other flowcharts in this description.

According to an optional next operation 747, an indication is recorded in a memory of an electrode becoming biased. This might have occurred, for example, per the previous operation 582 of FIG. 5.

FIG. 8 shows a flowchart segment 800 for describing additional optional operations according to embodiments. The additional optional operations of flowchart segment 800 can be added to other flowcharts in this description.

According to an optional operation 830, a query is issued to the person. The query can be issued when a parameter has reached or exceeded response-check threshold 220 of FIG. 2.

According to a next operation 840, it is inquired whether a preset acceptable input in response to the query has been received timely, for example within a preset time after the query has been issued. If yes, then the person can be presumed to not have had an SCA, and escalation of inquiry or perception of severity of their condition can be forestalled. If not, then further escalation is justified, and other measures can take place, such as biasing one or more electrodes, and so on.

Figure 9:
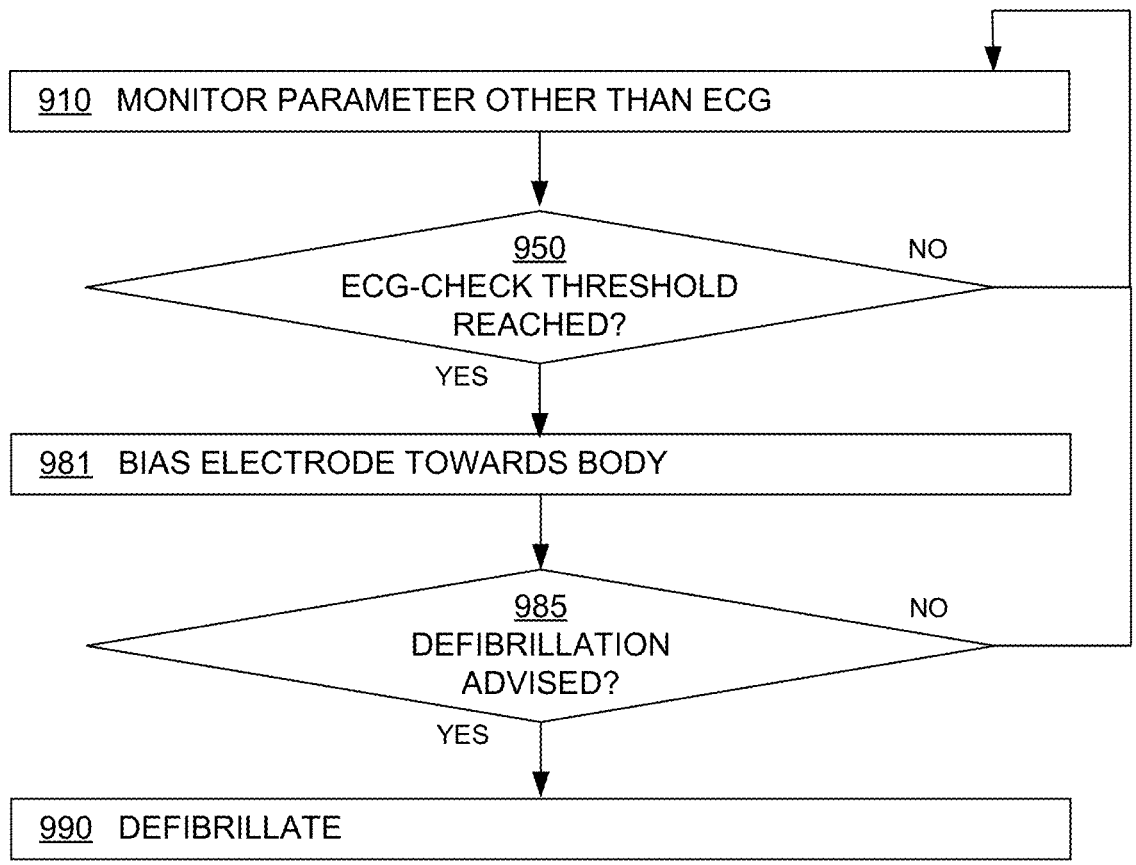
FIG. 9 is another flowchart for illustrating methods according to embodiments.

FIG. 9 shows a flowchart 900 for describing a method according to embodiments. According to an operation 910, a parameter is monitored that is not an ECG of the person.

According to a next operation 950, it is determined whether an ECG-check threshold 250 has been reached for the parameter. If not, execution returns to operation 910.

If yes, then according to a next operation 981, the certain electrode becomes biased towards the person's body against the support structure. As such, the certain electrode becomes less moveable with respect to the person's body than previously.

According to a next operation 985, it is inquired whether defibrillation is advised. If not, execution can return to operation 910. If yes, then according to a next operation 990, the person is defibrillated.

Figure 10:
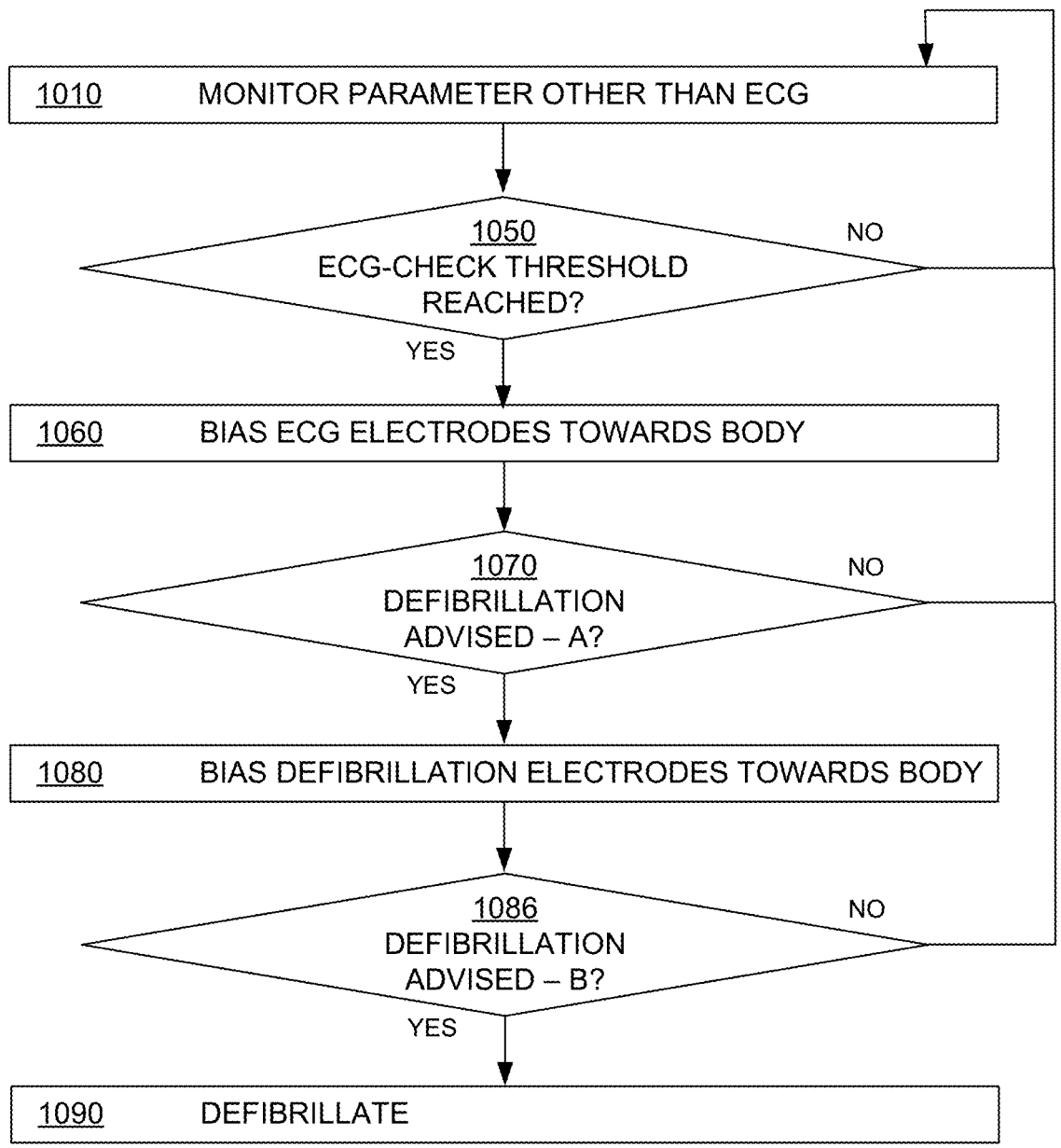
FIG. 10 is one more flowchart for illustrating methods according to embodiments.

FIG. 10 shows a flowchart 1000 for describing a method according to embodiments. Flowchart 1000 is for a device that has distinct ECG electrodes from defibrillation electrodes, with distinct respective biasing mechanisms. Unlike the usually large defibrillation electrodes, ECG electrodes maybe harder to aim to suitable locations on the person's skin.

According to an operation 1010, a parameter is monitored that is not an ECG of the person. According to a next operation 1050, it is determined whether an ECG-check threshold 250 has been reached for the parameter. If not, execution returns to operation 1010.

If yes, then according to a next operation 1060, the ECG electrodes become biased towards the person's body against the support structure. As such, the ECG electrodes become less moveable with respect to the person's body than previously.

According to a next operation 1070, it is first inquired whether defibrillation is likely advised. The first inquiry—also designated as "A" in the flowchart—of this operation 1070 is according to ECG readings received from the now biased ECG electrodes. The first inquiry of this operation 1070 can be more tentative than the upcoming inquiry. If not, execution can return to operation 1010.

If yes, then according to a next operation 1080, the defibrillation electrodes become biased towards the person's body against the support structure.

According to a next operation 1086, it is again inquired whether defibrillation is advised. The second inquiry—also designated as "B" in the flowchart—of this operation 1086 is according to ECG readings received from the now biased defibrillation electrodes and can be to determine whether threshold 285 has been reached or exceeded. If not, execution can return to operation 1010. If yes, then according to a next operation 1090, the person is defibrillated.

In the above, the order of operations is not constrained to what is shown, and different orders may be possible according to different embodiments. In addition, in certain embodiments, new operations may be added, or individual operations may be modified or deleted.

A person skilled in the art will be able to practice the present invention in view of this description, which is to be taken as a whole. Details have been included to provide a thorough understanding. In other instances, well-known aspects have not been described, in order to not obscure unnecessarily the present invention.

This description includes one or more examples, but that does not limit how the invention may be practiced. Indeed, examples or embodiments of the invention may be practiced according to what is described, or yet differently, and also in conjunction with other present or future technologies.

One or more embodiments described herein may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "computer-readable media" includes computer-storage media. For example, computer-storage media may include, but are not limited to, magnetic storage devices (e.g., hard disk, floppy disk, and magnetic strips), optical disks (e.g., compact disk [CD] and digital versatile disk [DVD]), smart cards, flash memory devices (e.g., thumb drive, stick, key drive, and SD cards), and volatile and nonvolatile memory (e.g., RAM and ROM).

Other embodiments include combinations and sub-combinations of features described herein, including for example, embodiments that are equivalent to: providing or applying a feature in a different order than in a described embodiment, extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

In the claims appended herein, the inventor invokes 35 U.S.C. § 112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. § 112, paragraph 6.

What is claimed is:

1. A wearable medical system configured to be worn by a person, comprising:
    a support structure configured to be worn by the person;
    a monitoring device configured to monitor at least one physiological parameter of the person, wherein the at least one physiological parameter includes an electrocardiogram (ECG) reading of the person;
    an electrode coupled to the support structure;
    an energy storage device configured to store an electric charge for use in delivering a shock to the person through the electrode; and
    a biasing mechanism comprising at least one of an inflatable device, a hydraulic device, an electromagnetic device, and/or a screw gun device, the biasing mechanism configured to transition from the unbiased state to the biased state responsive to a value of the at least one physiological parameter reaching a threshold;
    wherein in the unbiased state the electrode is more movable with respect to a body of the person and in the biased state the electrode is less movable with respect to the body of the person.

2. The wearable medical system of claim 1, wherein the electrode further comprises an adhesive material configured to adhere to the person in response to the biasing mechanism transitioning to the biased state.

3. The wearable medical system of claim 2, wherein the electric charge is to be delivered as one or more defibrillation shocks.

4. The wearable medical system of claim 2, wherein the electric charge is to be delivered as one or more pacing pulses.

5. The wearable medical system of claim 2, wherein the electric charge is delivered to the person when the biasing mechanism is in the biased state.

6. The wearable medical system of claim 1, wherein the energy storage device comprises a capacitor to be charged to a selected energy level in response to the electrode transitioning to the biased state in preparation for a sudden discharge of the electric charge.

7. The wearable medical system of claim 6, wherein the capacitor is charged to a lower energy level to avoid wasting energy.

8. The wearable medical system of claim 6, wherein the capacitor is charged to a right amount of energy to avoid wasting energy.

9. The wearable medical system of claim 2, wherein the adhesive material is deployed right before the biasing mechanism transitions to the biased state.

10. The wearable medical system of claim 1, wherein the biasing mechanism is configured to transition from the unbiased state to the biased state responsive to the ECG reading indicating a shockable event.

11. A wearable medical system, comprising:
   a support structure configured to be worn by the person;
   a monitoring device configured to monitor a plurality of physiological parameters of the person, wherein the plurality of physiological parameters include an electrocardiogram (ECG) reading of the person and a pulse reading of the person;
   an electrode coupled to the support structure;
   an energy storage device configured to store an electric charge, and to deliver the electric charge to the person through the electrode in response to a shockable event based at least in part on the plurality of physiological parameters indicating the shockable event.

12. The wearable medical system of claim 11, further comprising a biasing mechanism to change from an unbiased state to a biased state in response to a value of the at least one physiological parameter, the biasing mechanism comprising at least one of an inflatable device, a hydraulic device, and electromagnetic device, and/or a screw gun device.

13. The wearable medical system of claim 12, wherein the electrode is in loose contact with a body of the person in the unbiased state.

14. The wearable medical system of claim 12, wherein the electrode makes electrical contact with a body of the person in the biased state.

15. The wearable medical system of claim 11, wherein the plurality of physiological parameters further comprises a heart sound of the person in addition to the ECG reading and the pulse reading.

16. The wearable medical system of claim 11, wherein the energy storage device includes a capacitor that is charged to a lower energy level to avoid wasting energy in response to at least one of the plurality of physiological parameters meeting a defibrillation advised threshold.

17. A method to operate a wearable medical system, comprising:
   monitoring at least one physiological parameter of a person wearing the wearable medical system, wherein the at least one physiological parameter includes an electrocardiogram (ECG) reading of the person;
   in response to the at least one physiological parameter meeting a threshold value, causing a biasing mechanism to transition from an unbiased state to a biased state, wherein an electrode of the wearable medical system is in loose contact with a body of the person when the biasing mechanism is in the unbiased state, and the electrode is in electrical contact with the body of the person when the biasing mechanism is in the biased state; and
   charging a capacitor of the wearable medical system to a lower energy level in response to biasing the electrode to the biased state in preparation for a sudden discharge of an electric charge to the person through the electrode.

18. The method of claim 17, wherein biasing the electrode occurs in response to the ECG reading meeting a threshold.

19. The method of claim 17, wherein the ECG reading is obtained in response to the least one physiological parameter meeting an ECG-check threshold.

20. The method of claim 17, further comprising discharging the electric charge through the electrode to the person as one or more pacing pulses.

* * * * *